US012637398B2

(12) United States Patent
Zalutsky et al.

(10) Patent No.: US 12,637,398 B2
(45) Date of Patent: May 26, 2026

(54) RADIOHALOGEN PROSTHETIC MOIETIES AND RADIOLABELED BIOMOLECULES

(71) Applicant: DUKE UNIVERSITY, Durham, NC (US)

(72) Inventors: Michael Rod Zalutsky, Chapel Hill, NC (US); Ganesan Vaidyanathan, Chapel Hill, NC (US); Darryl Lynn McDougald, Durham, NC (US)

(73) Assignee: Duke University, Durham, NC (US)

(*) Notice: Subject to any disclaimer, the term of this patent is extended or adjusted under 35 U.S.C. 154(b) by 974 days.

(21) Appl. No.: 17/776,330

(22) PCT Filed: Nov. 11, 2020

(86) PCT No.: PCT/US2020/060032
§ 371 (c)(1),
(2) Date: May 12, 2022

(87) PCT Pub. No.: WO2021/096968
PCT Pub. Date: May 20, 2021

(65) Prior Publication Data
US 2023/0002293 A1 Jan. 5, 2023

Related U.S. Application Data

(60) Provisional application No. 62/934,740, filed on Nov. 13, 2019.

(51) Int. Cl.

| | |
|---|---|
| ***C07B 59/00*** | (2006.01) |
| ***A61K 47/68*** | (2017.01) |
| ***C07F 7/22*** | (2006.01) |
| ***C07K 16/30*** | (2006.01) |
| *A61K 39/00* | (2006.01) |

(52) U.S. Cl.
CPC .......... *C07B 59/00* (2013.01); *A61K 47/6869* (2017.08); *C07F 7/2208* (2013.01); *C07K 16/3069* (2013.01); *A61K 2039/505* (2013.01); *C07K 2317/34* (2013.01); *C07K 2317/56* (2013.01); *C07K 2317/77* (2013.01)

(58) Field of Classification Search
CPC ... C07B 59/00; A61K 47/6869; C07F 7/2208; C07K 16/3069
USPC .......................................................... 424/1.69
See application file for complete search history.

(56) References Cited

FOREIGN PATENT DOCUMENTS

| | | | | |
|---|---|---|---|---|
| WO | WO-8912631 A1 * | 12/1989 | | A61K 51/1045 |
| WO | WO-2010147666 A1 * | 12/2010 | | C07K 5/0215 |
| WO | WO 2018/178936 | 10/2018 | | |

OTHER PUBLICATIONS

Ali et al. Anal. Chem. 2011, 83, 2877-2882. (Year: 2011).*
Ali et al. Anal. Chem. 2011, 83 (Supp.), S1-S44. (Year: 2011).*
Ogan et al., "A Specific Radioimmunoassay for the Measurement of Gadoteridol, a Contrast Agent for Magnetic Resonance Imaging in Biological Fluids," *Journal of Pharmaceutical Sciences, American Chemical Society and American Pharmaceutical Association*, vol. 82, No. 5, 1993, pp. 475-479.
Banerjee, "Therapeutic Radiopharmaceuticals: Linking Chemistry, Radiochemistry, and Practical Applications", *Chemical Reviews*, 2014, vol. 115, No. 8, pp. 2934-2974.
D'Huyvetter et al . . . "I-labeled Anti-HER2 Camelid sdAB as a Theranostic Tool in Cancer Traeatment", *Clinical Cancer Research*, 2017, vol. 23, No. 21, pp. 6616-6628.
Vaidyanathan et al., "SIB-DOTA: A Trifunctional Prosthetic Group Potentially Amenable for Multi-Modal Labeling that Enhances Tumor Uptake of Internalizing Monoclonal Antibodies," *Bioorganic & Medicinal Chemistry*, 2012, vol. 20, No. 24, pp. 6929-6939.

* cited by examiner

*Primary Examiner* — Michael G. Hartley
*Assistant Examiner* — Sean R Donohue
(74) *Attorney, Agent, or Firm* — Womble Bond Dickinson (US) LLP

(57) ABSTRACT

The application is drawn to radiohalogen prosthetic moieties and precursors thereof and to radiolabeled biomolecules comprising such radiohalogen prosthetic moieties. The biomolecules have an affinity for particular types of cells and may specifically bind a certain cell, such as a cancer cell. Relevant biomolecules include antibodies, monoclonal antibodies, antibody fragments, peptides, other proteins, nanoparticles, aptamers, and pharamacological moieties used to target prostate-specific membrane antigen (PSMA).

18 Claims, No Drawings

RADIOHALOGEN PROSTHETIC MOIETIES AND RADIOLABELED BIOMOLECULES

CROSS-REFERENCE TO RELATED APPLICATIONS

The present application is a U.S. National Stage of International Patent Application PCT/US2020/060032 filed Nov. 11, 2020 and claims priority to U.S. Provisional Patent Application No. 62/934,740, filed Nov. 13, 2019. The disclosures of each of the applications noted above are incorporated herein by reference in their entireties.

FIELD OF THE INVENTION

The present invention is drawn to radiohalogen prosthetic moieties useful for radiolabeling biomolecules and to methods of preparing such radiohalogen prosthetic moieties and radiolabeled biomolecules. The disclosure also provides precursors of such radiohalogen prosthetic moieties. The radiohalogen prosthetic moieties can effectively retain radioactivity from biomolecules that become internalized within cells, rendering such moieties and corresponding radiolabeled biomolecules useful in the diagnosis and treatment of disease, particularly cancer.

BACKGROUND

Radioiodination is one of the simplest ways to radiolabel a biomolecule. Several radioisotopes of iodine are available for imaging and targeted radiotherapy of cancer. Radioisotopes of iodine are supplied as alkaline solutions and iodine is present in these in an oxidation state of −1 ($I^-$; iodide). The standard method for biomolecule radioiodination requires oxidation of the iodine to the +1 oxidation state for electrophilic substitution into tyrosine amino acids present in biomolecules such as antibodies, other proteins and peptides. Challenges of thus radioiodinated monoclonal antibodies (mAbs) and peptides include their instability in vivo to proteolysis inside cells after internalization, deiodination, and as a consequence of both processes, loss of radioactivity from tumor cells. It is widely recognized that radioiodinated antibodies and peptides are proteolytically degraded inside cells after internalization (which can occur as a consequence of binding to receptors and certain antigens), to radioiodotyrosine that is efficiently exported from the cells by membrane amino acid transporters. Released radioiodotyrosine is deiodinated by deiodinases found in tissues and the free radioiodine redistributes and accumulates in organs with sodium iodide symporter expression, particularly the thyroid, stomach, and salivary glands. Thus, the amount of radiolabel that is retained in tumors is diminished and concomitantly, the uptake of radioactivity in normal tissues is increased.

One of the disadvantages of antibodies is their long half-life in the bloodstream, which results in high background levels after systemic administration and, consequently, in low tumor to background ratios. Moreover, conventional antibodies have a rather slow diffusion into solid tumors, which prevents them from reaching and binding to receptor/antigen in the entire tumor mass homogeneously.

While some prosthetic agents have been identified in the art, they are unstable and hard to produce in commercial quantities. Moreover, the uptake of antibodies into tumor cells, particularly brain metastases, is low due to the size of the antibodies, which is particularly problematic for tumors in the brain because of delivery restrictions imposed by the blood brain barrier. Therefore, there is a need for further prosthetic agents that can be used to radiolabel biomolecules for targeted radiotherapies and imaging applications.

SUMMARY OF THE INVENTION

The invention is drawn to prosthetic agents, precursors thereof, and compositions for radiolabeling biomolecules (also referred to as macromolecules) with radioactive halogen atoms, and in particular, with radioactive iodine. Advantageously, such methods, compounds, and compositions may minimize loss of the radioactive halogen due to dehalogenation in vivo, preserve the biological activity of the biomolecule, maximize retention in diseased cells, such as cancer cells, and/or minimize the retention of radioactivity in normal tissues after in vivo administration.

The biomolecules have an affinity for particular types of cells. That is, the biomolecules may specifically bind a certain cell, such as a cancer cell. Certain compositions of the invention include the radiolabeled biomolecules. Such biomolecules include antibodies, monoclonal antibodies, antibody fragments, peptides, other proteins, nanoparticles and aptamers. Such examples of biomolecules for purposes of the invention include, diabodies, scFv fragments, DARPins, fibronectin type III-based scaffolds, affibodies, VHH molecules (also known as single domain antibody fragments (sdAb) and nanobodies), nucleic acid or protein aptamers, and nanoparticles. Additionally, larger molecules such as proteins >50 kDa including antibodies, monoclonal antibodies, chimeric antibodies, humanized antibodies, and $F(ab')_2$ fragments can be used in the methods disclosed herein. In addition, nanoparticles with a size less than 50 nm can be used in the methods disclosed herein. The principles disclosed herein are, in some embodiments, particularly relevant to VHH molecule and other types of small protein constructs (although it is not limited thereto), as will be described more thoroughly herein.

As such, the disclosure provides such radiolabeling moieties (referred to herein as "radiohalogen prosthetic moieties"), as well as precursors to afford such prosthetic moieties (referred to herein as "radiohalogen precursors"). The disclosure further provides radiolabeled macromolecules (e.g., biomolecules) comprising such radiohalogen prosthetic moieties and one or more macromolecules. In some such embodiments, these radiolabeled macromolecules are targeted radiotherapeutic agents. The prosthetic moieties and radiolabeled macromolecules of the invention are useful, e.g., for diagnosing disease and for targeted radiotherapy.

The present disclosure includes, without limitation, the following embodiments.

Embodiment 1: A radiohalogen prosthetic moiety or precursor thereof, according to the following formula:

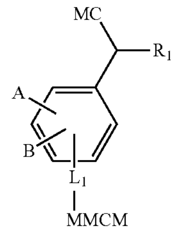

wherein: MC is a polydentate chelate moiety; $R_1$ is H, an ester, or a carboxylic acid; A is —$R_2$-$R_3$—Y or Y; B is H, an alkoxy group, or a non-radioactive halogen; $R_2$ is a direct bond, an alkyl group, or an oxygen-containing moiety (e.g., —O—, —O—$CH_2$—, —O—$CH_2CH_2$—, and the like); $R_3$ is a direct bond or an aromatic moiety; Y is a radioactive halogen or a moiety that can be converted to a radiohalogen (also referred to herein as a "precursor" to a radioactive halogen); MMCM is a macromolecule conjugation moiety; and $L_1$ is a direct bond or linker.

Embodiment 2: The radiohalogen prosthetic moiety or precursor of the preceding embodiment, wherein MC is a cyclic polydentate chelate moiety.

Embodiment 3: The radiohalogen prosthetic moiety or precursor of Embodiment 1, wherein MC is an acyclic polydentate chelate moiety.

Embodiment 4: The radiohalogen prosthetic moiety or precursor of Embodiment 1, wherein MC is a modified DOTA moiety.

Embodiment 5: The radiohalogen prosthetic moiety or precursor of the preceding embodiment, wherein MC is DOTA-tris(t-Bu ester) or DOTA-tris(COOH).

Embodiment 6: The radiohalogen prosthetic moiety or precursor of Embodiment 1, wherein MC is a modified NOTA moiety.

Embodiment 7: The radiohalogen prosthetic moiety or precursor of the preceding embodiment, wherein MC is NOTA-bis(t-bu ester) or NOTA-bis(COOH).

Embodiment 8: The radiohalogen prosthetic moiety or precursor of any preceding embodiment, wherein MC comprises a metal.

Embodiment 9: The radiohalogen prosthetic moiety or precursor of the preceding embodiment, wherein the metal is selected from the group consisting of nonradioactive metals (including, e.g., lutetium, yttrium, indium, or gallium) and radioactive metals (including, e.g., $^{177}Lu$, $^{64}Cu$, $^{67}Cu$, $^{111}In$, $^{90}Y$, $^{225}Ac$, $^{213}Bi$, $^{212}Pb$, $^{212}Bi$, $^{67}Ga$, $^{68}Ga$, $^{89}Zr$, and $^{227}Th$).

Embodiment 10: The radiohalogen prosthetic moiety or precursor of any of Embodiments 1-7, wherein MC does not comprise a metal.

Embodiment 11: The radiohalogen prosthetic moiety or precursor of any preceding embodiment, wherein MC is connected through a nitrogen atom present thereon or wherein MC is connected through a backbone carbon.

Embodiment 12: The radiohalogen prosthetic moiety or precursor of Embodiment 1, represented by the following formula:

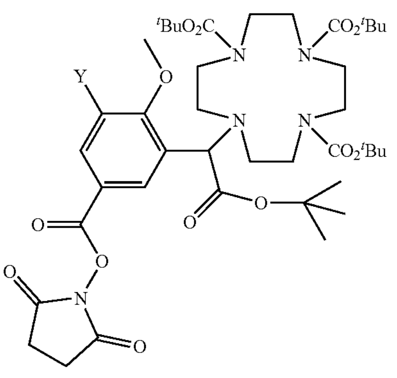

Embodiment 13: The radiohalogen prosthetic moiety or precursor of Embodiment 1, represented by the following formula:

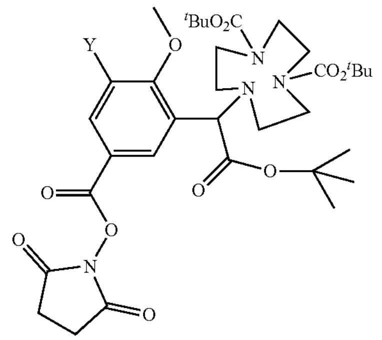

Embodiment 14: The radiohalogen prosthetic moiety or precursor of Embodiment 1, represented by the following formula:

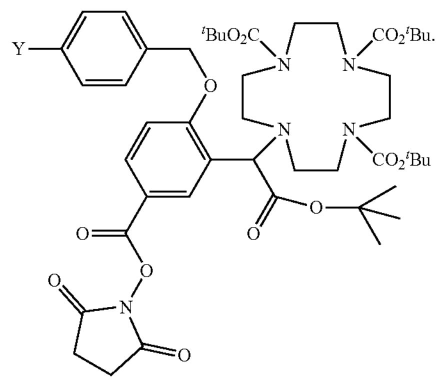

Embodiment 15: The radiohalogen prosthetic moiety or precursor of Embodiment 1, represented by the following formula:

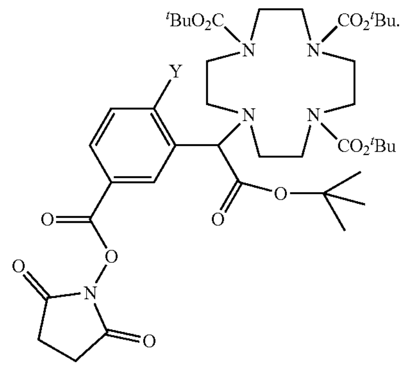

Embodiment 16: The radiohalogen prosthetic moiety or precursor of Embodiment 1, represented by the following formula:

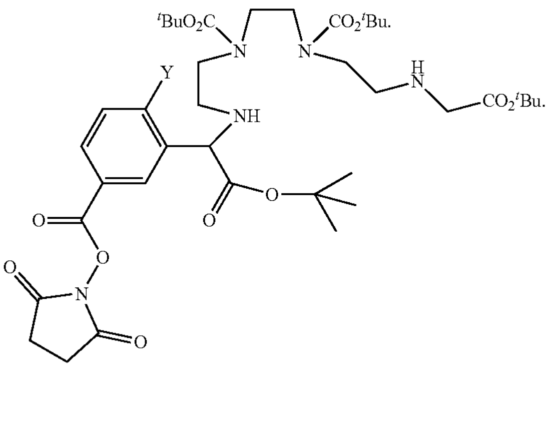

Embodiment 17: The radiohalogen prosthetic moiety or precursor of Embodiment 1, represented by the following formula:

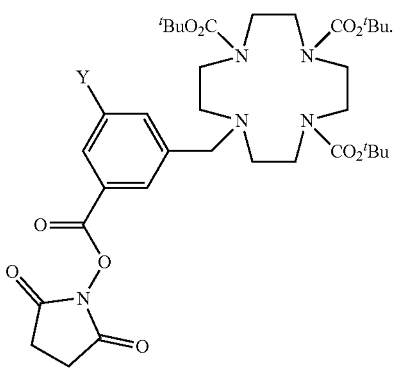

Embodiment 18: The radiohalogen prosthetic moiety or precursor of Embodiment 1, represented by the following formula:

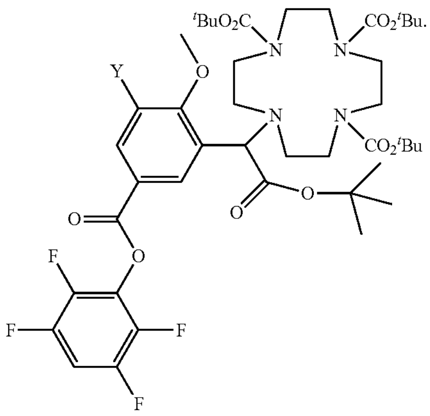

Embodiment 19: The radiohalogen prosthetic moiety or precursor of Embodiment 1, represented by the following formula:

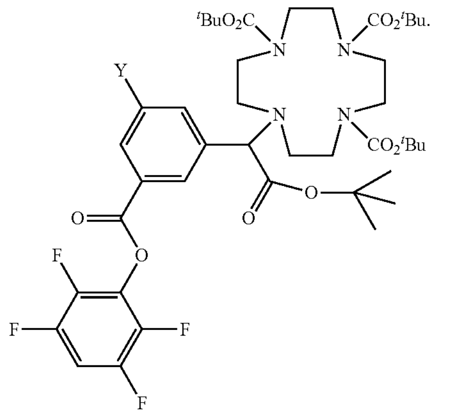

Embodiment 20: The radiohalogen prosthetic moiety or precursor of Embodiment 1, represented by the following formula:

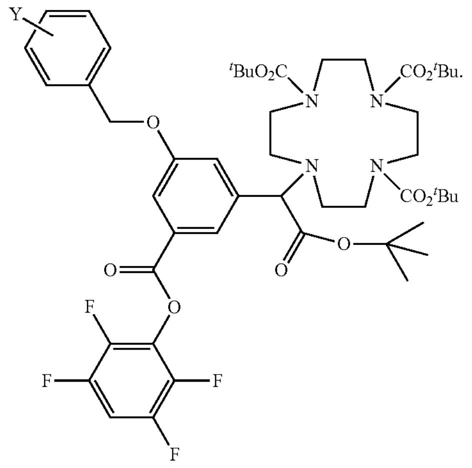

Embodiment 21: The radiohalogen prosthetic moiety or precursor of Embodiment 1, represented by the following formula:

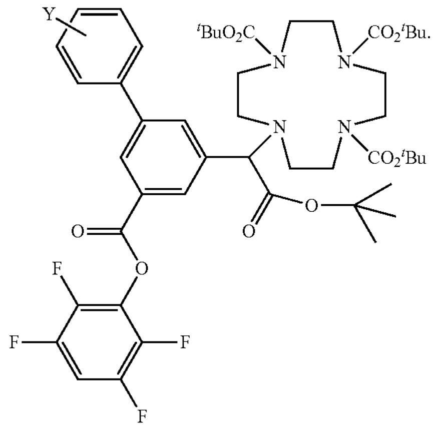

Embodiment 22: The radiohalogen prosthetic moiety or precursor of any preceding embodiment, wherein Y is selected from the group consisting of $^{18}F$, $^{75}Br$, $^{76}Br$, $^{77}Br$, $^{123}I$, $^{124}I$, $^{125}I$, $^{131}I$, and $^{211}At$.

Embodiment 23: The radiohalogen prosthetic moiety or precursor of any of Embodiments 1-22, wherein Y is selected from the group consisting of a trialkyl tin moiety, trialkyl silicon moiety, trialkyl germanium moiety, a HgX moiety (X=halogen, $CH_3COO$, $CF_3COO$ etc), a $Tl(OCOCF_3)_2$ moiety, boronic acid ($B(OH)_2$), Bpin (pivaloyl boronate), aryl iodonium salt, and iodonium ylide among others (including, e.g., a diazonium salt or a triazene).

Embodiment 24: The radiohalogen prosthetic moiety or precursor of any of Embodiments 12-23, with no metal complexed within the polydentate chelate moiety.

Embodiment 25: The radiohalogen prosthetic moiety or precursor of any of Embodiments 12-23, further comprising a metal complexed within the polydentate chelate moiety.

Embodiment 26: The radiohalogen prosthetic moiety or precursor of any of Embodiments 12-23, wherein the metal is selected from the group consisting of nonradioactive metals (including, e.g., lutetium, yttrium, indium, or gallium) and radioactive metals (including, e.g., $^{177}Lu$, $^{65}Cu$, $^{67}Cu$, $^{111}In$, $^{90}Y$, $^{225}Ac$, $^{213}Bi$, $^{212}Pb$, $^{212}Bi$, $^{67}Ga$, $^{68}Ga$, $^{89}Zr$, and $^{227}Th$).

Embodiment 27: The radiohalogen prosthetic moiety or precursor of any one of the preceding embodiments, wherein one or more of the $CO_2{}^tBu$ groups shown is deprotected (i.e., replaced with a COOH group), including wherein all of the $CO_2{}^tBu$ groups shown are deprotected.

Embodiment 28: A radiolabeled biomolecule or intermediate, comprising the radiohalogen prosthetic moiety or precursor of any preceding embodiment attached to a biomolecule.

Embodiment 29: The radiolabeled biomolecule or intermediate of the preceding embodiment, wherein the biomolecule is selected from the group consisting of an antibody, an antibody fragment, a VHH molecule, an aptamer or variations thereof.

Embodiment 30: The radiolabeled biomolecule or intermediate of any preceding embodiment, wherein the biomolecule is a VHH.

Embodiment 31: The radiolabeled biomolecule or intermediate of the preceding embodiment, wherein said VHH targets HER2.

Embodiment 32: The radiolabeled biomolecule or intermediate of Embodiment 28, wherein the biomolecule comprises a carbamate- or urea-containing pharmacological moiety.

Embodiment 33: The radiolabeled biomolecule or intermediate of the preceding embodiment, wherein the carbamate- or urea-containing pharmacological moiety is a moiety used to target PSMA on prostate cancer.

It is noted that, in the specific structures shown in Embodiments 12-21, the type of chelating moiety shown is not intended to be limiting, e.g., where the radiohalogen prosethetic moiety or precursor is shown to comprise a N-hydroxysuccinimide (NHS) ester, analogues comprising a tetrafluorophenol (TFP) ester, an isothiocyanate group, a maleimide group (or other chelating moiety) in place of the NHS ester are also encompassed herein. Similarly, where the radiohalogen prosethetic moiety or precursor is shown to comprise a TFP ester, analogues comprising an NHS ester, an isothiocyanate group, a maleimide group (or other chelating moiety) in place of the TFP ester are also encompassed herein.

It is further noted that, in certain embodiments, aromatic/aryl rings are incorporated within the disclosed moieties. The term "aryl" as used herein means a stable monocyclic, bicyclic, or tricyclic carbon ring of up to 8 members in each ring, wherein at least one ring is aromatic as defined by the Hückel 4n+2 rule. In the embodiments depicted herein, the aromatic/aryl rings are generally shown as being homoaromatic/homoaryl; however, the disclosure is also intended to encompass heteroaromatic/heteroaryl rings. As such, one or more (e.g., 1-4) of the carbon atoms depicted in the aromatic/aryl rings of the formulas provided herein can, in some embodiments, be replaced with a heteroatom selected from O, S, and N. In some preferred embodiments, such rings can comprise one heteroatom that is N. Exemplary aryl groups include, but are not limited to, phenyl, naphthyl, tetrahydronaphthyl, and biphenyl, and exemplary aromatic groups include, but are not limited to, benzene, indole, furan, pyridine, and pyrazine, as well as substituted derivatives thereof.

These and other features, aspects, and advantages of the disclosure will be apparent from a reading of the following detailed description. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise. Other aspects and advantages of the present invention will become apparent from the following.

DETAILED DESCRIPTION

The disclosure generally provides certain radiohalogen prosthetic moieties, precursors thereof, and radiolabeled macromolecules comprising the radiohalogen prosthetic moieties. Certain relevant chemical and biological components of these moieties, precursors, and radiolabeled macromolecules are disclosed in U.S. Pat. No. 9,839,704 to Zalutsky et al., which is incorporated herein by reference in its entirety.

As referenced, for example, in International Patent Application Publication No. WO2018/178936, which is incorporated herein by reference in its entirety, certain exemplary radiohalogen precursors and radiohalogen prosthetic moieties can be defined according to the following formula:

$$MC\text{-}Cm\text{-}L_4\text{-}Cm\text{-}T \quad \text{(Formula X)}$$

wherein the substituents are defined as referenced therein (generally, with "MC" representing a polydentate metal chelate moiety, "Cm" representing a conjugating moiety, e.g., thiourea, amide, or thioether, "$L_4$" representing a bond, a substituted or unsubstituted alkyl chain, a substituted or unsubstituted alkenyl chain, a substituted or unsubstituted alkynyl chain, optionally having NH, CO, or S on one or both termini, or a polyethylene glycol (PEG) chain, and "T" representing a radiohalogen prosthetic moiety or its precursor). The present application provides certain modifications and highlighted features of various prosthetic moieties and radiolabeled macromolecules comprising such moieties as well as precursors thereof, such as those disclosed in the referenced documents, as will be outlined more fully herein below.

The present specification specifically provides radiohalogen precursor moieties and radiohalogen prosthetic moieties that are somewhat similar in structure to those of Formula X, but which do not comprise the Cm-$L_4$-Cm linker functionality. According to the present disclosure, radiohalogen precursor moieties and radiohalogen prosthetic moieties are provided with a simplified structure, referred to herein as Formula A (shown below)

MC-T (Formula A)

MC is a polydentate metal chelate moiety. MC can be any polydentate chelate moiety and may be cyclic or acyclic. The composition of MC can vary. MC can be either uncomplexed (lacking a metal) or complexed with the stable (nonradioactive) or radioactive form of a metal. In some embodiments, the metal is a metal of any charge, with a +2, +3, or +4 charge preferred. In certain embodiments, the metal is a trivalent metal ($M^{+3}$) such as lutetium, yttrium, indium, actinium, or gallium and in certain embodiments, specific radioactive metals that can be complexed with the MC include, but are not limited to, radioactive metals selected from the group consisting of $^{177}$Lu, $^{64}$Cu, $^{67}$Cu, $^{111}$In, $^{90}$Y, $^{225}$Ac, $^{213}$Bi, $^{212}$Pb, $^{212}$Bi, $^{67}$Ga, $^{68}$Ga, $^{89}$Zr, and $^{227}$Th. It is noted that this list is not exhaustive and, although these exemplified radioactive and non-radioactive metals are trivalent, certain MCs that may be used according to the present invention may bind metals of other valencies, and such metals and MCs containing such metals are also encompassed herein.

In some embodiments, MC is a macrocyclic ligand, consisting of a ring containing 8 or more atoms, bearing at least 3 negatively charged substituents such as carboxyl or phosphonate groups. Exemplary macrocyclic ligands suitable as the MC group include 1,4,7,10-tetraazacyclododecane-1,4,7,10-tetraacetic acid (DOTA), 1,4,7-triazacyclononane-1,4,7-triacetic acid (NOTA), 1,4,8,11-tetraazacyclotetradecane-1,4,8,11-tetraacetic acid (TETA), and 1,4,7-triazacyclononane-1,4,7-tri(methylene phosphonic acid) (NOTP). In other embodiments, MC is MeO-DOTA, as disclosed in Gali et al., Anticancer Research (2001), 21(4A), 2785-2792), which is incorporated herein by reference.

The present disclosure specifically recognizes advantages of employing a functionalized MC group, e.g., a modified DOTA or a modified NOTA. One exemplary modified DOTA is DOTA-tris(t-Bu ester), i.e., DOTA comprising tert-butyl acetate groups associated with each nitrogen atom other than the nitrogen atom when it is used to connect to "T." Such a compound, suitable for reaction to provide MC-T is also referred to as tri-tert-butyl 1,4,7,10-tetraazacyclododecane-1,4,7-tricarboxylate. Upon removal of the tert-butyl protecting groups, a deprotected form is provided, which can be referred to as 1,4,7,10-tetraazacyclododecane-1,4,7-tricarboxylic acid. A further modified DOTA that may find use in certain embodiments of the disclosure is an acyclic analogue, e.g., an acyclic analogue of DOTA or an acyclic analogue of a modified DOTA. One exemplary tert-butyl acetate-functionalized acyclic DOTA that can be reacted to form MC-T is tert-butyl (2-(2-((2-aminoethyl)(tert-butoxycarbonyl)amino)ethyl)(tert-butoxycarbonyl)amino)ethyl)glycinate. Upon removal of the tert-butyl protecting groups, a deprotected form is provided, which can be referred to as (2-((2-((2-aminoethyl)(carboxy)amino)ethyl)(carboxy)amino)ethyl)glycine. Similarly, in some embodiments, a modified analogue of NOTA is employed, which comprises tert-butyl acetate groups associated with each nitrogen atom other than the nitrogen atom when it is used to connect to "T." Such a modified NOTA can be di-tert-butyl 1,4,7-triazonane-1,4-dicarboxylate, which can be reacted via the nitrogen atom without a tert-butyl group attached thereto to give MC-T.

Although not intending to be limited by theory, it is believed that such acetate substituents (or acetic acid substituents, upon deprotection of the modified DOTA/NOTA MC groups) provide some degree of stabilization of the DOTA/NOTA (or analogue thereof) chelation moiety. It is understood that, in all figures herein providing a tert-butyl acetate group associated with the MC group, although shown with t-butyl, the deprotected form (comprising an acetic acid group in place of the tert-butyl acetate group) is also intended to be encompassed herein.

Certain such modified "MC" groups are shown below in Formulas B-1, B-2, and B-3, respectively, with one feasible point of attachment to "T" shown on each depicted "MC" moiety, providing relevant radiohalogen precursor moieties, and radiohalogen prosthetic moieties, and radiolabeled biomolecules comprising the same.

(Formula B-1)

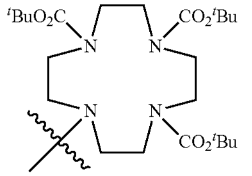

(Formula B-2)

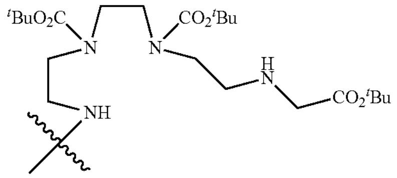

(Formula B-3)

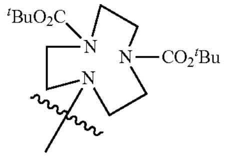

According to the present disclosure, MC is connected to the remainder of the prosthetic/precursor moiety (comprising "T") via any relevant atom, e.g., via a carbon or nitrogen associated with the MC (although not limited thereto) to give corresponding radiohalogen precursors and prosthetic moieties. For the modified DOTA and NOTA groups referenced herein, MC can be advantageously connected to T via a nitrogen present on the modified DOTA/NOTA (as shown in Formulas B-1, B-2, and B-3 above) or via other positions on the MC (including, e.g., via one of the MC backbone carbons).

T is a radiohalogenated template or radiohalogen precursor template. T can be, for example, a compound of Formula C as shown below (a compound comprising a MMCM, as will be described in further detail below), where its connection to MC is shown by the wavy line. Typically, in the disclosed structures, T is directly bonded to the MC, i.e., with a direct bond between the carbon atom shown adjacent to $R_1$ and a moiety on MC (e.g., where MC is DOTA/NOTA or a modified DOTA/NOTA, the carbon atom shown below can be directly bonded to a nitrogen atom of the backbone DOTA/NOTA structure).

(Formula C)

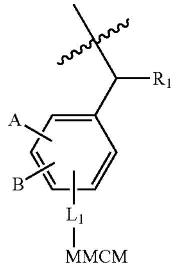

In Formula C, the following definitions are applicable:

$R_1$=H, an ester, or a carboxylic acid.

A is $R_2$-$R_3$—Y or Y.

B is H, an alkoxy (e.g., methoxy, ethoxy, propoxy, or butoxy) group, or a halogen (e.g., a non-radioactive halogen, such as selected from the group consisting of Cl, F, I, and Br).

$R_2$=a direct bond, an alkyl group, or an oxygen-containing moiety. Certain examples of "oxygen-containing moieties" as provided herein include, but are not limited to: —O—, —O—$CH_2$—, —O—$CH_2CH_2$—, and the like.

$R_3$=a direct bond, an alkyl group, or an aromatic moiety (e.g., a phenyl ring).

Y=a) a radioactive halogen (e.g., such as selected from $^{18}F$, $^{75}Br$, $^{76}Br$, $^{77}Br$, $^{123}I$, $^{124}I$, $^{125}I$, $^{131}I$, and $^{211}At$ (such that the depicted moiety is a radiohalogen prosthetic moiety); or b) a precursor to a radioactive halogen (such that the depicted moiety is a suitable precursor for radiohalogenation, also referred to herein as a "radiohalogen precursor moiety"). Suitable precursors for radiohalogenation can vary and include, e.g., alkyl metal moieties comprising three C1-6 alkyl group ligands on the metal (e.g., trialkyl tin moieties, e.g., $Bu_3Sn$ or $Me_3Sn$, trialkyl silicon moieties, and trialkyl germanium moieties). Other suitable precursors for radiohalogenation include, but are not limited to, HgX moieties (X=halogen, $CH_3COO$, $CF_3COO$, etc.), $Tl(OCOCF_3)_2$ moieties, boronic acid ($B(OH)_2$), Bpin (pivaloyl boronate), aryl iodonium salt, iodonium ylide, diazonium salts, triazene, and the like, which can be further treated to provide a radiohalogen prosthetic moiety.

MMCM=macromolecule conjugation moiety to couple the compound/radical of Formula C to a macromolecule.

$L_1$=a direct bond or linker.

In certain embodiments, $R_2$ is —O—$CH_2$— and $R_3$ is a phenyl ring, such that $R_2$-$R_3$ is a benzyloxy group attached to the central phenyl ring of Formula C. The positions of the substituents on the phenyl ring relative to one another can vary. $L_1$-MMCM on the aromatic ring relative to the other substituents (A, B, and the connection to MC) can vary. In certain embodiments, the $L_1$-MMCM group is meta to the connection to MC. The central phenyl ring of the compound, in some embodiments, comprises no substituents ortho to $L_1$-MMCM (such that the carbon to which $L_1$-MMCM is connected is ortho to two non-substituted carbon atoms). In some preferred embodiments, A is ortho to the carbon connected to MC. Where A is ortho to the carbon connected to MC, in some such embodiments, B is ortho to the A substituent, and is H. In other preferred embodiments, A is meta to the carbon connected to MC. Where A is meta to the carbon connected to MC, in some such embodiments, B is ortho to the carbon connected to MC (and meta to the A substituent), and in certain embodiments, B is alkoxy (e.g., methoxy).

MMCM can vary and can be any component suitable for connection to a biomolecule. In some embodiments, MMCM is an active ester. An active ester is defined herein as an ester that can be conjugated with amine groups present on a macromolecule/biomolecule (e.g., a peptide or protein) under mild conditions, i.e., conditions that will not result in loss of biological function of the macromolecule/biomolecule. Exemplary such MMCM groups include, but are not limited to, a N-hydroxysuccinimide (NHS) ester or a tetrafluorophenol (TFP) ester, an isothiocyanate group, or a maleimide group. Such MMCMs generally result in random (non-site specific) labeling of amine groups on the protein or peptide. In other embodiments, MMCM provides for site-specific conjugation to be performed using an enzyme such as Sortase, which results in conjugation to only one site on the protein (either the N-terminus or the C-terminus of the protein). In the case of Sortase, MMCM is, e.g., the tripeptide GlyGlyGly. Enzymes that may be employed for obtaining suitable conjugation are not particularly limited and include, for example, translugaminase, lipoic acid ligase, farnesyl transferase, and many more, such as those disclosed, e.g., in Massa et al., *Exp. Opin. Drug Del.* 2016, 13(8), pp. 1149-1163; Zhang et al., *Chem. Soc. Rev.* 2018, 47, pp. 9106-9136; Falck et al., *Antibodies* 2018, 7(4), pp. 1-19; and van Berkel et al., *Drug Disc. Today: Technologies* 2018, 30, pp. 3-10, which are all incorporated herein by reference in their entireties.

MMCM can be directly bound to the aromatic ring ($L_1$=a direct bond) or can be bound to the aromatic ring through a linker ($L_1$). $L_1$ can be, e.g., a spacer such as a substituted or unsubstituted alkyl chain, a substituted or unsubstituted alkenyl chain, a substituted or unsubstituted alkynyl chain, or a short polyethylene glycol (PEG) chain (1-10 ethylene glycol units).

According to the present disclosure, certain structural features associated with such radiohalogen precursors and prosthetic moieties have been identified as serving various advantageous functions, as will be outlined more thoroughly herein below. Radiohalogen precursors and prosthetic moieties, as well as radiolabeled biomolecules are provided herein which include various combinations of these identified structural features.

In one embodiment, $R_1$ is advantageously an ester group, e.g., $CO_2{}^tBu$, as shown in Formula C-1, below. In such embodiments, this $R_1$ group between the aromatic ring on "T" and the "MC" group can provide further stabilization of the metal complex, particularly after deprotection, giving free COOH at this site.

(Formula C-1)

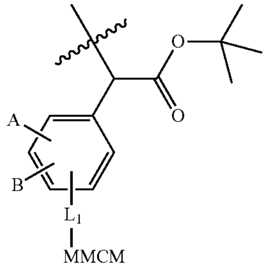

In one embodiment, the central aromatic ring of T is functionalized with an alkoxy group as substituent B and, in particular, a methoxy ($OCH_3$) group. Although this alkoxy group can be present at varying locations on the phenyl ring, the alkoxy group is advantageously on a carbon ortho to the carbon to which the $CHR_1$-MC group is attached, such that the alkoxy is in relatively close proximity to the MC moiety. It has surprisingly been found that this group can provide additional stabilization of the metal complex (e.g., modified DOTA group or NOTA group), particularly upon deprotection of the metal complex ester substituents. Advantageously, such compounds including an alkoxy group on the phenyl ring have four substituents on the aromatic ring. For example, see Formula C-2, below.

(Formula C-2)

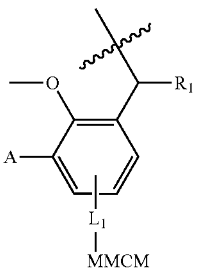

In some embodiments, the halogenation site or precursor moiety is placed on an aromatic ring that is attached (directly or indirectly) to the central aryl ring (e.g., including, but not limited to, being connected to the central aryl ring via an O-alkyl-moiety), as shown in Formula C-3. Although the location of the halogen or trialkyl metal moiety on the phenyl ring can vary, in certain embodiments, the halogen or trialkyl metal moiety is para to the connection to the remainder of the molecule. In some such embodiments as shown in Formula C-3, B is H. In another embodiment, as shown in Formula C-4, the halogen site or precursor moiety is on an aromatic ring connected to the central aryl ring, where the aromatic ring is directly bonded to the central aryl ring, as shown. In some such embodiments as shown in Formula C-4, B is H.

It is noted that, in embodiments wherein the halogenation site or precursor moiety is on an aromatic ring attached to the central aryl ring, the aromatic ring may comprise no other substituents, or in some embodiments, may comprise one or more additional substituents at varying positions with respect to the halogenation site or precursor moiety. For example, in some embodiments, the aromatic ring further comprises a guanidinomethyl. Thus, although, e.g., Formulas C-3 and C-4 below are shown with an aromatic ring substituted only with I, the disclosure is not limited thereto, and other substituents may be present on that ring in various embodiments. In one particular embodiment, a moiety of Formula C-3 is provided wherein the aryl ring is substituted with both I and a guanidinomethyl group.

(Formula C-3)

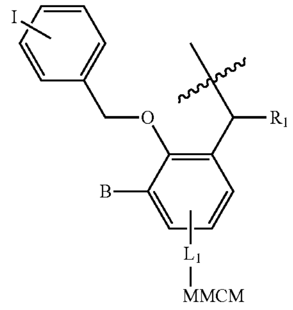

-continued (Formula C-4)

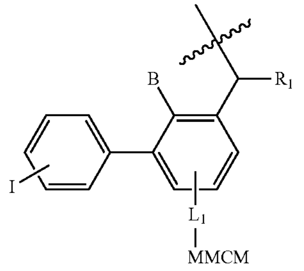

In some embodiments, the halogenation site/precursor moiety is directly on the central aryl ring (e.g., connected via a direct bond), as explicitly shown in Formulas C-5 and C-6. In some such embodiments as shown in Formula C-5, B is H. In Formula C-5 the iodination site is proximal the chelation ester; these types of structures may advantageously enable weak charge stabilization to the chelation moiety. In some such embodiments as shown in Formula C-6, B is advantageously $OCH_3$.

(Formula C-5)

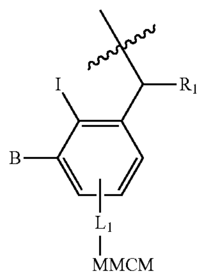

(Formula C-6)

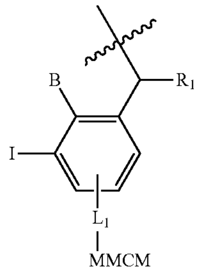

In one specific embodiment, a DOTA-SIB radiohalogen prosthetic moiety is provided, according to Formula D-1, below.

(Formula D-1)

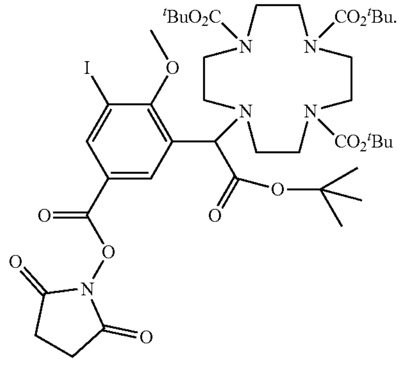

As shown, this radiohalogen prosthetic moiety of Formula D-1 comprises a single carbon between the functionalized phenyl ring of T and a nitrogen on the modified DOTA chelate moiety (MC). In Formula D-1, the $CO_2{}^t$Bu group on the carbon between the functionalized phenyl ring of T and the nitrogen on the modified DOTA chelate moiety provides further charge stabilization of the chelation complex (particularly after deprotection, giving free COOH groups on the modified DOTA). In addition, the methoxy substituent on the central aryl ring provides additional charge stabilization for the modified DOTA chelation moiety. In the radiohalogen prosthetic moiety of Formula D-1, the halogenation site is directly on the central aryl (benzene) ring.

Formula D-2 provides a similar NOTA-SIB hybrid radiohalogen prosthetic moiety.

(Formula D-2)

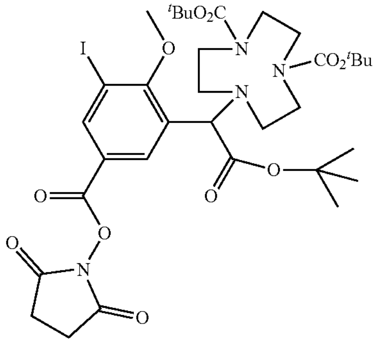

In another specific embodiment, a DOTA-SIB radiohalogen prosthetic moiety is provided, according to Formula D-3, below.

(Formula D-3)

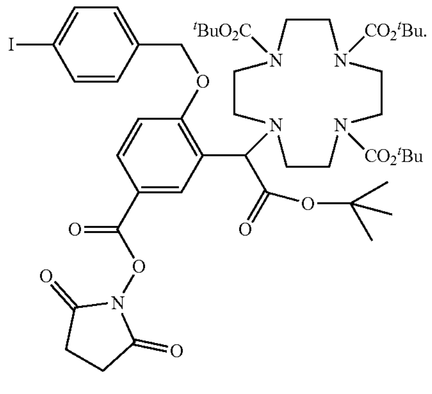

As shown, this radiohalogen prosthetic moiety of Formula D-3 comprises a single carbon between the functionalized phenyl ring of T and a nitrogen on the modified DOTA chelate moiety (MC). In Formula D-3, the $CO_2{}^t$Bu group on the carbon between the functionalized phenyl ring of T and the nitrogen on the modified DOTA chelate moiety provides further charge stabilization of the chelation complex (particularly after deprotection, giving free COOH groups on the modified DOTA). The O-alkyl subunit immediately proximal to the central aryl ring provides additional charge stabilization to the chelation moiety MC. The halogen in this Formula D-3 structure is placed on an aromatic ring substituted on the O-alkyl-subunit, rather than on the central aromatic ring.

Again, as referenced above with respect to general Formula C-3, in further embodiments, the compound of Formula D-3 may further comprise one or more additional substituents on the aromatic ring substituted on the O-alkyl-subunit. For example, in one embodiment, the aromatic ring substituted on the O-alkyl-subunit of Formula D-3 comprises, in addition to the I shown, a guanidinomethyl group (which can be ortho or meta to the I substituent on the ring). One specific example is shown below as Formula D-3', where X and Y can be placed in any of the five positions on the aromatic ring. If X is an iodine radioisotope or another radiohalogen (or a precursor thereto), Y is guanidinomethyl, and vice versa. The N-hydroxysuccinimidyl ester can, as referenced throughout, be replaced with other groups, e.g., a TFP ester group.

(Formula D-3)

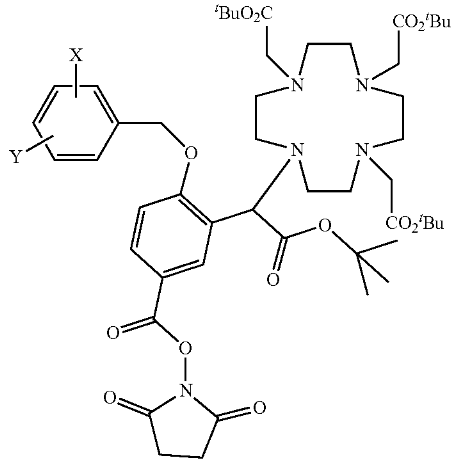

In a further specific embodiment, a DOTA-SIB radiohalogen prosthetic moiety is provided, according to Formula D-4, below.

(Formul D-4)

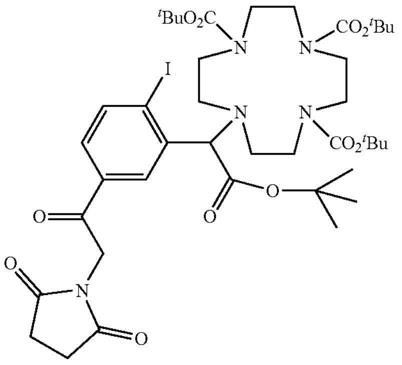

As shown, this radiohalogen prosthetic moiety of Formula D-4 comprises a single carbon between the functionalized phenyl ring of T and a nitrogen on the modified DOTA chelate moiety (MC). In Formula D-4, the $CO_2{}^t$Bu group on the carbon between the functionalized phenyl ring of T and the nitrogen on the modified DOTA chelate moiety provides further charge stabilization of the chelation complex (particularly after deprotection, giving free COOH groups on the functionalized DOTA). The halogen in Formula D-4 is proximal to the modified DOTA, enabling weak charge stabilization to the metal complex.

In a further specific embodiment, a DOTA-SIB radiohalogen prosthetic moiety is provided, according to Formula D-5, below.

(Formula D-5)

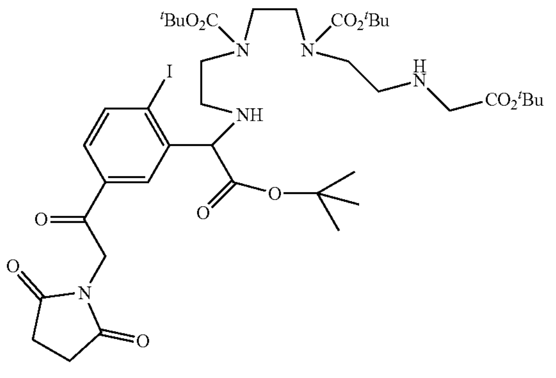

As shown, this radiohalogen prosthetic moiety of Formula D-5 is comparable in structure to that of Formula D-4 but comprises an acyclic modified DOTA (rather than the cyclic form in Formula D-4).

In some specific embodiments, $L_1$-MC is a tetrafluorophenol (TFP) ester, e.g., as shown in Formulas D-6 to D-8, below. Again, Formula D-7 can be modified, e.g., as described above with respect to Formula D-3, to comprise one or more additional substituents on the —O-alkyl-phenyl group in addition to the I substituent illustrated (e.g., a guanidnomethyl group).

(Figure D-6)

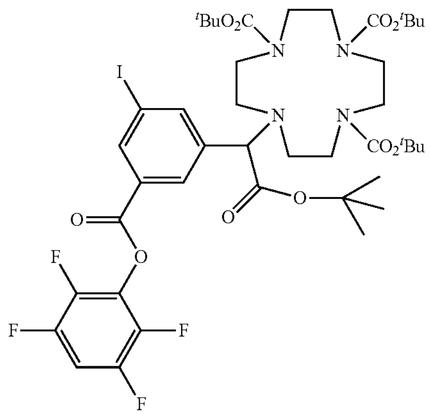

-continued (Figure D-7)

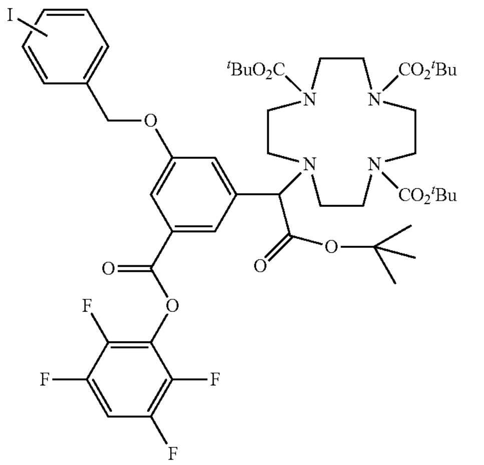

(Figure D-8)

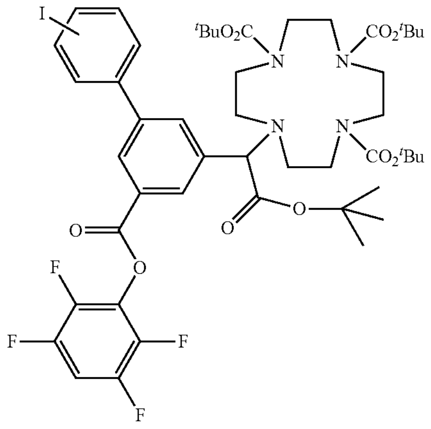

Although, as shown in Formulas D1 to D8, an ester-containing $R_1$-substituent is commonly preferred, e.g., a $CO_2{}^tBu$ group, in other embodiments, a radiohalogen prosthetic moiety or precursor thereof is provided wherein $R_1$ is H, as shown in Formula D-9, below. In some embodiments, such a moiety can be prepared in fewer steps than other comparable compounds (e.g., those comprising an ester group at the $R_1$ position).

(Formula D-9)

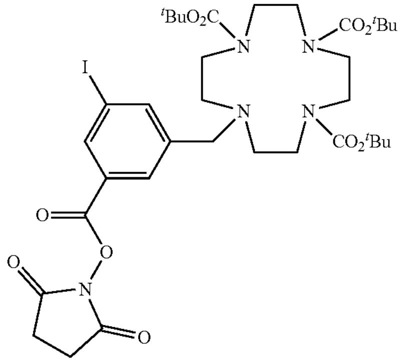

It is understood that the disclosure encompasses, in addition to the general formulas above and the specific Formulas D1-D6 (which are depicted as radiohalogen prosthetic moieties comprising a radioactive iodine), analogues of D1-D6 with other halogens, e.g., where the radioiodine (I) is replaced with another radioactive halogen (e.g., including, but not limited to, $^{18}F$), as well as analogues that serve as precursors to the moieties of Formulas D1-D6 (i.e., radiohalogen precursor moieties), e.g., where the I is replaced with a precursor moiety such as an alkyl metal moiety (including, but not limited to, $Bu_3Sn$, e.g., $^{t}Bu_3Sn$). As referenced above, the precursor may comprise, e.g., an alkyl metal moiety such as a trialkyl tin moiety, trialkyl silicon moiety, trialkyl germanium moiety, a HgX moiety (X=halogen, $CH_3COO$, $CF_3COO$ etc), or a $Tl(OCOCF_3)_2$ moiety, boronic acid ($B(OH)_2$), Bpin (pivaloyl boronate), aryl iodonium salt, and iodonium ylide among others (including, e.g., diazonium salt or a triazene), which can be further treated to provide a radiohalogen prosthetic moiety.

The disclosure further provides methods of providing radiohalogen prosthetic moieties and radioactive (e.g., radioactive iodine)-labeled prosthetic moieties that can be conjugated with biomolecules (via the MMCM), e.g., in a site-specific manner (falling within the formulas referenced herein above). It further provides resulting radioactive (e.g., iodine radionuclides, bromine radionuclides, $^{18}F$, or $^{211}At$)-labeled biomolecules. Relevant biomolecules include those generally disclosed in International Patent Application Publication No. WO2018/178936, which is incorporated herein by reference in its entirety. The biomolecule can vary widely. In some embodiments, the biomolecule is selected from the group consisting of an antibody, an antibody fragment, a VHH molecule, an aptamer or variations thereof. One particular examples is a VHH, e.g., such as a VHH that targets HER2. In some embodiments, the biomolecule comprises a carbamate or urea-containing pharmacological moiety (e.g., as used to target prostate-specific membrane antigen (PSMA). Such radioactive-labeled biomolecules can be provided according to the present disclosure, e.g., by replacing the protein/peptide with an appropriate carbamate or urea and using the same labeling template as described for, e.g., proteins. See, for example, Yang et al., *J. Med. Chem.* 2016, 59, pp. 206-218; Chen et al., J. Med, Chem. 2008, 51, pp. 7933-7943; and Fiber et al., *J. Nucl., Med.* 2017, pp. 67S-76S, which are all incorporated herein by reference in their entireties.

The disclosure further provides a pharmaceutical composition comprising a radiolabeled biomolecule as disclosed herein (e.g., the labeled biomolecules described/shown above) in association with one or more pharmaceutically acceptable adjuvants, diluents, and/or carriers. In a further aspect of the disclosure is provided a method of treatment for cancer, comprising administering to an individual in need thereof an effective amount of a radiolabeled biomolecule as disclosed herein and/or an effective amount of a pharmaceutical composition as disclosed herein.

The following examples are offered by way of illustration and not by way of limitation.

EXAMPLE 1: Preparation of tri-tert-butyl 2,2',2"-(10-(2-(tert-butoxy)-1-(5-(((2,5-dioxopyrrolidin-1-yl)oxy)carbonyl)-2-methoxy-3-(tributylstannyl)phenyl)-2-oxoethyl)-1,4,7,10-tetraazacyclododecane-1,4,7-triyl)triacetate a. Benzyl 4-(benzyloxy)-3-methylbenzoate

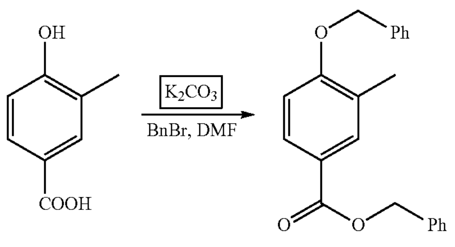

To a round bottom flask was added 4-hydroxy-3-methylbenzoic acid (2.0 g, 1 eq., 13 mmol), potassium carbonate (7.3 g, 4.0 eq., 53 mmol), benzyl bromide (22 g, 16 mL, 10 eq., 0.13 mol) and N,N-Dimethylformamide (75 mL). The reaction mixture was heated at 80° C. for a period of 16 hours at which time the mixture was cooled to rt and partitioned with water and ethyl acetate. The organics were separated and dried over $MgSO_4$ and concentrated to dryness. The crude oil was purified using a 50 g SNAP ULTRA® silica gel column (hexanes: EA, 9:1) to give benzyl 4-(benzyloxy)-3-methylbenzoate (4.0 g, 92%) as a pure oil. LRMS (M+H) (333), (M+Na) (355).

b. 4-(Benzyloxy)-3-methylbenzoic Acid

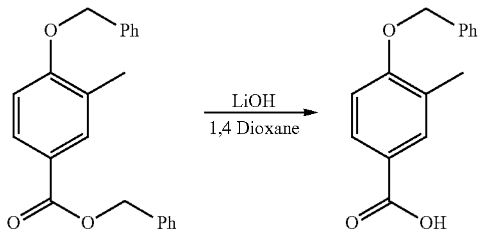 [SMILES: Cc1cc(C(=O)OCc2ccccc2)ccc1OCc1ccccc1 ; "LiOH" ; Cc1cc(C(=O)O)ccc1OCc1ccccc1]

To a 100 ml round bottom flask was added benzyl 4-(benzyloxy)-3-methylbenzoate (4.0 g, 1 eq., 12 mmol), 1,4-Dioxane (25 mL), water (25 mL) and lithium hydroxide (1.2 g, 4.00 eq., 48 mmol). The cloudy mixture was allowed to react at 25° C. for 16 hours at which time the mixture was concentrated to one half volume in vacuo using a rotary evaporator. The resulting crude material was diluted with water and extracted with ether. The ether layer was discarded, the aqueous layer was cooled to 0-5° C., and the mixture was made acidic using concentrated HCl. The resulting cloudy white mixture was extracted with ethyl acetate, ethyl acetate solution, dried over $MgSO_4$ and concentrated to dryness to give 4-(benzyloxy)-3-methylbenzoic acid (2.7 g, 93%) as a mostly pure white solid. The product was used without further purification. LRMS (M−H) (241).

c. 2-(Trimethylsilyl)ethyl 4-(benzyloxy)-3-methylbenzoate

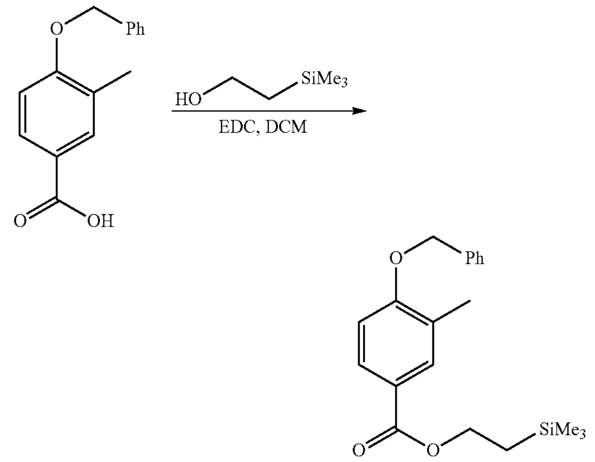

4-(Benzyloxy)-3-methylbenzoic acid (2.6 g, 1 eq., 11 mmol), DMAP (0.13 g, 0.1 eq., 1.1 mmol), EDC (3.1 g, 1.5 eq., 16 mmol) and dichloromethane (75 mL) were added to a 100 ml round bottom flask and the resulting solution was allowed to stir at rt for about 5 minutes. To this stirring solution, 2-(trimethylsily)ethan-1-ol (1.9 g, 1.5 eq., 16 mmol) was added and the reaction was stirred at 25° C. for a period of 16 hours. The reaction mixture was partitioned between saturated water and $CH_2Cl_2$. The organics were separated and dried over anhydrous $Na_2SO_4$. The volatiles were concentrated and chromatographed using a 50 g BIOTAGE SNAP ULTRA column (hexanes: EtOAc (1:1) to afford 2-(trimethylsilyl)ethyl 4-(benzyloxy)-3-methylbenzoate (3.0 g, 82%) a clear oil. LRMS (M+Na) ($365^+$).

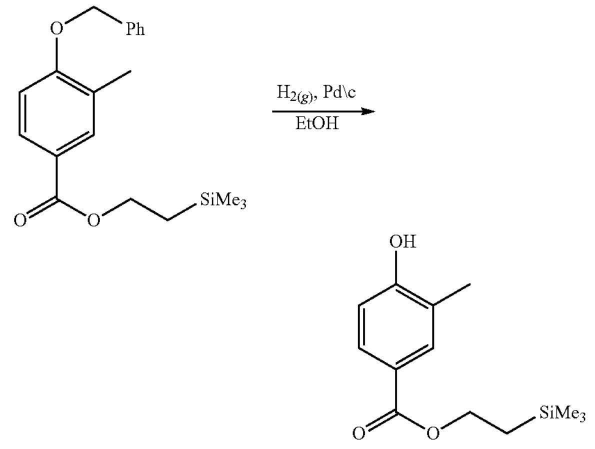

d. 2-(Trimethylsilyl)ethyl 4-hydroxy-3-methylbenzoate

To a round bottom flask was added a solution of 2-(trimethylsilyl)ethyl 4-(benzyloxy)-3-methylbenzoate (2.0 g, 1 eq., 5.8 mmol) in 50 mL ethanol. The homogeneous solution was then degassed under house vacuum for a period of 5 minutes. The solution was then mixed with palladium on carbon (0.20 g, 0.032 eq., 0.19 mmol) and degassing was repeated. After 5 minutes, the mixture was purged with Hydrogen gas using a balloon. The reaction was allowed to proceed for a period of 2 hours with occasional refilling of the balloon. The reaction was shown to be complete by TLC and the mixture was degassed under vacuum. The reaction was then purged with Argon and the palladium catalyst was filtered off using Celite. The Celite was washed with MeOH and the filtrate was concentrated to dryness resulting in 2-(trimethylsilyl)ethyl 4-hydroxy-3-methylbenzoate (1.3 g, 88%) as an oily solid. LRMS (M+H) (253+), (M−H) (251).

e. 2-(Trimethylsilyl)ethyl 4-acetoxy-3-methylbenzoate

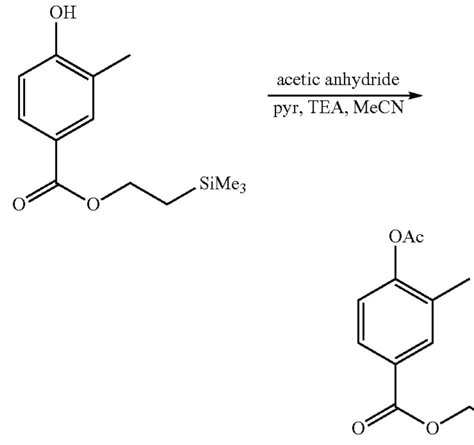

To a round bottom flask was added TEA (1.2 g, 1.6 mL, 2 eq., 12 mmol), 2-(trimethylsilyl)ethyl 4-hydroxy-3-methylbenzoate (1.5 g, 1 eq., 5.9 mmol), pyridine (1.4 g, 1.4 mL, 3 eq., 18 mmol), and acetonitrile (50 mL). The reaction mixture was stirred at rt and charged with acetic anhydride (2.4 g, 2.2 mL, 4 eq., 24 mmol). The reaction was allowed to stir at rt for 16 hours and was partitioned between water and ethyl acetate. The organics were separated and dried over $MgSO_4$ and concentrated to dryness. The crude oil was purified using a 25 g SNAP ULTRA® silica gel column (hexanes: EA, 9:1) to give 2-(trimethylsilyl)ethyl 4-acetoxy-3-methylbenzoate (1.5 g, 86%) as a pure oil. LRMS (M+Na) (317).

f. 2-(Trimethylsilyl)ethyl 4-acetoxy-3-(bromomethyl)benzoate

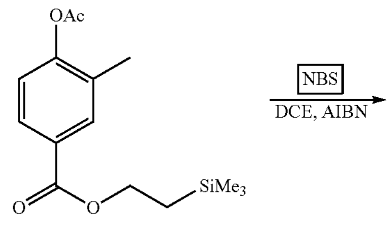

-continued

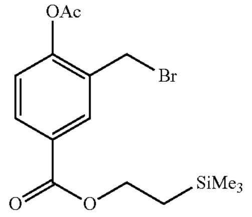

To an oven dried round bottom flask was added 2-(trimethylsilyl)ethyl 4-acetoxy-3-methylbenzoate (1.5 g, 1 eq., 5.1 mmol), 1,2-dichloroethane (50 mL) and NBS (1.8 g, 2.0 eq., 10 mmol). The resulting solution was stirred at rt for a period of 5 minutes. This mixture was heated to 90° C. and mixed with AIBN (0.17 g, 0.2 eq., 1.0 mmol) and the reaction was allowed to react for 2.5 hours. After 2.5 hours, the reaction was concentrated to dryness to afford an oily solid. The crude product was chromatographed using a Biotage 10 g SNAP ULTRA column (hexanes: EtOAc 10:1) to give 2-(trimethylsilyl)ethyl 4-acetoxy-3-(bromomethyl) benzoate (1.8 g, 95%) as a low melting solid in about an 70% purity. The material is inherently unstable and was used as such for the next reaction.

g. 2-(Trimethylsilyl)ethyl 4-acetoxy-3-(2-(tert-butoxy)-2-oxoethyl)benzoate

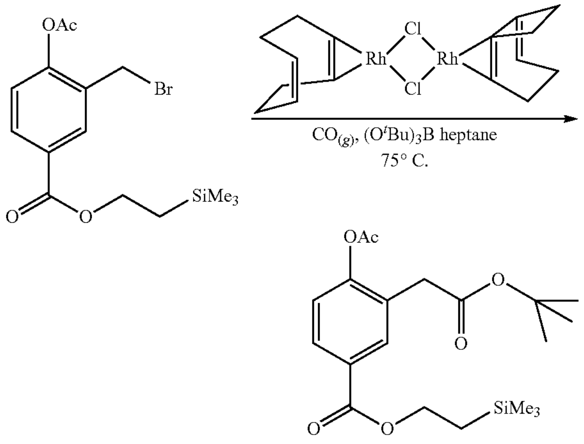

To a round bottom flask was added 2-(trimethylsilyl)ethyl 4-acetoxy-3-(bromomethyl)benzoate (1.8 g, 1 eq., 4.8 mmol), heptane (100 mL) and tri-tert-butyl borate (3.3 g, 3.0 eq., 14 mmol), and the solution was purged with argon for 5 minutes. The flask was then charged with chloro(1,5-cyclooctadiene)rhodium(I) dimer (0.24 g, 0.1 eq., 0.48 mmol) and purged with additional argon. The solution was then purged with carbon monoxide for 2 minutes and sealed using a rubber septum. The reaction flask was fitted with a balloon filled with carbon monoxide and heated at 75° C. for a period of 24 hours. The reaction mixture was filtered through celite and concentrated to dryness and the crude black oil was purified using a 25 g SNAP Ultra Biotage column (hexanes: EtOAc (5:1)) to give 2-(trimethylsilyl) ethyl 4-acetoxy-3-(2-(tert-butoxy)-2-oxoethyl)benzoate (562 mg, 30%) as an oil. LRMS (M+H) (395), (M+Na) (417).

h. 2-(Trimethylsilyl)ethyl 3-(2-(tert-butoxy)-2-oxoethyl)-4-hydroxybenzoate

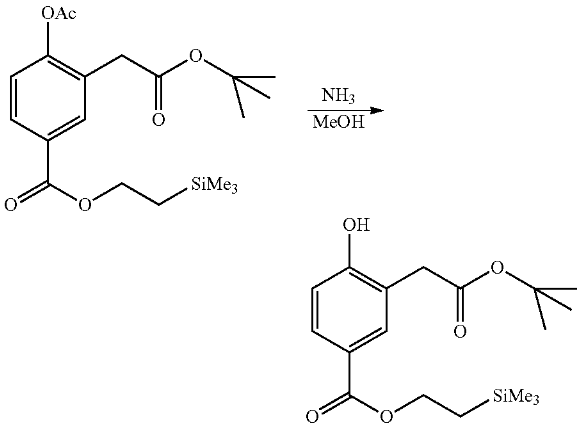

A round bottom flask was charged with 2-(trimethylsilyl) ethyl 4-acetoxy-3-(2-(tert-butoxy)-2-oxoethyl)benzoate (500 mg, 1 eq., 1.27 mmol) and methanol (50 mL). The solution was cooled to 0-5° C. and purged for 3 minutes with ammonia gas. The flask was fitted with a balloon filled with argon and the reaction was stirred for a period of 4.0 hours. The reaction was shown to be complete by tlc analysis after 4 hours and the reaction mixture was concentrated to dryness to give 2-(trimethylsilyl)ethyl 3-(2-(tert-butoxy)-2-oxoethyl)-4-hydroxybenzoate (466 mg, 104%) which was carried over to the next step without purification. LRMS (M+Na) (375), (M−H) (351).

i. 2-(Trimethylsily)ethyl 3-bromo-5-(2-(tert-butoxy)-2-oxoethyl)-4-hydroxybenzoate

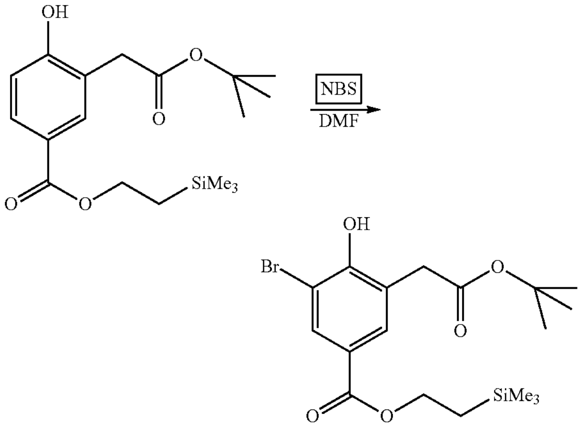

To a round bottom flask was added 2-(trimethylsilyl)ethyl 3-(2-(tert-butoxy)-2-oxoethyl)-4-hydroxybenzoate (400 mg, 1 eq., 1.13 mmol) and N,N-dimethylformamide (20 mL) and the reaction mixture was cooled to 0-5° C. The reaction solution was then mixed with NBS (606 mg, 3.0 eq., 3.40 mmol) and the reaction was stirred at rt for 3.0 hours. The reaction was shown to be complete by tlc analysis and it was then partitioned between EtOAc and water. The EtOAc layer was separated and dried over $MgSO_4$, and concentrated to dryness to give 2-(trimethylsilyl)ethyl 3-bromo-5-(2-(tert-butoxy)-2-oxoethyl)-4-hydroxybenzoate (533 mg, 109%) as a crude solid with some residual DMF. LRMS (M+Na) (453, 455), (M−H) (429, 431).

j. 2-(trimethylsilyl)ethyl 3-bromo-5-(2-(tert-butoxy)-2-oxoethyl)-4-methoxybenzoate

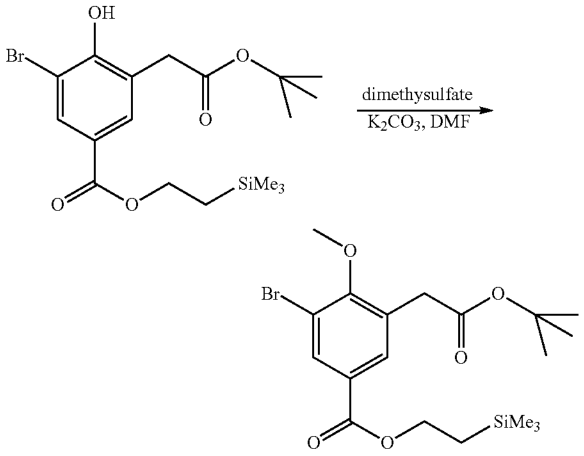

A round bottom flask was charged with 2-(trimethylsilyl) ethyl 3-bromo-5-(2-(tert-butoxy)-2-oxoethyl)-4-hydroxybenzoate (533 mg, 1 eq., 1.24 mmol), potassium carbonate (854 mg, 5.0 eq., 6.18 mmol), dimethyl sulfate (468 mg, 354 μL, 3.0 eq., 3.71 mmol) and N,N-Dimethylformamide (20 mL). The reaction mixture was heated at 50° C. for a period of 2 hours at which time the mixture was cooled to rt and partitioned between water and ethyl acetate. The organics were separated, dried over $MgSO_4$ and concentrated to dryness. The crude oil was purified using a 10 g SNAP ULTRA® silica gel column (hexanes: EA, 9:1) to give 2-(trimethylsilyl)ethyl 3-bromo-5-(2-(tert-butoxy)-2-oxoethyl)-4-methoxybenzoate (301 mg, 54.7%) as an oil. LRMS (M+Na) (467, 469).

k. Tri-tert-butyl 2,2',2"-(10-(1-(3-bromo-2-methoxy-5-((2-(trimethylsilyl)ethoxy)carbonyl)phenyl)-2-(tert-butoxy)-2-oxoethyl)-1,4,7,10-tetraazacyclododecane-1,4,7-triyl)triacetate

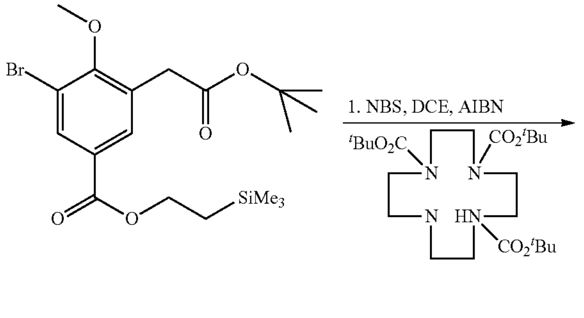

-continued

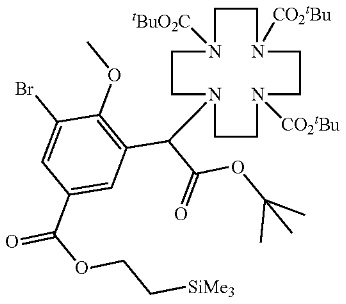

A round bottom flask was charged with 2-(trimethylsilyl) ethyl 3-bromo-5-(2-(tert-butoxy)-2-oxoethyl)-4-methoxybenzoate (300 mg, 1 eq., 674 μmol), NBS (180 mg, 1.5 eq., 1.01 mmol), AIBN (11.1 mg, 0.1 eq., 67.4 μmol) and 1,2-Dichloroethane (20 mL) and the reaction mixture was heated to reflux for a period of 1.0 hour. The reaction mixture was then concentrated to dryness and the resulting oily solid was mixed with ether and the insolubles were filtered off. The filtrate was concentrated to give a crude oil which was a mixture of 2-(trimethylsilyl)ethyl 3-bromo-5-(1-bromo-2-(tert-butoxy)-2-oxoethyl)-4-methoxybenzoate and starting material. This material was mixed with tri-tert-butyl 2,2',2"-(1,4,7,10-tetraazacyclododecane-1,4,7-triyl) triacetate (347 mg, 1 eq., 674 μmol), acetonitrile (20 mL) and potassium carbonate (372 mg, 4.0 eq, 2.69 mmol). The mixture was then heated at 50° C. for 16 hours. The reaction mixture was filtered to remove excess potassium carbonate and the crude product, obtained by the evaporation of acetonitrile from the filtrate was dissolved in methylene chloride and filtered over a bed of silica gel using a 9:1 solution of dichloromethane and MeOH. The solution was concentrated to give the desired product tri-tert-butyl 2,2',2"-(10-(1-(3-bromo-2-methoxy-5-((2-(trimethylsilyl) ethoxy)carbonyl)phenyl)-2-(tert-butoxy)-2-oxoethyl)-1,4,7,10-tetraazacyclododecane-1,4,7-triyl)triacetate (445 mg, 69.0%) as a crude solid. LRMS (M+H), (957, 959), (M+Na), (979, 981).

l. Tri-tert-butyl 2,2',2"-(10-(2-(tert-butoxy)-1-(2-methoxy-3-(tributylstannyl)-5-((2-(trimethylsilyl) ethoxy)carbonyl)phenyl)-2-oxoethyl)-1,4,7,10-tetraazacyclododecane-1,4,7-triyl)triacetate

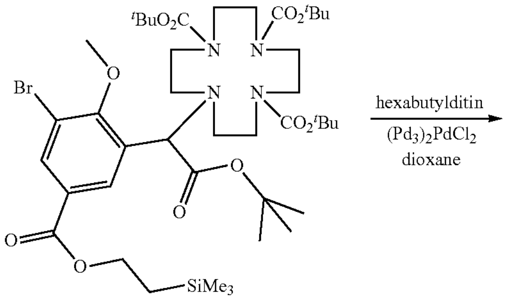

-continued

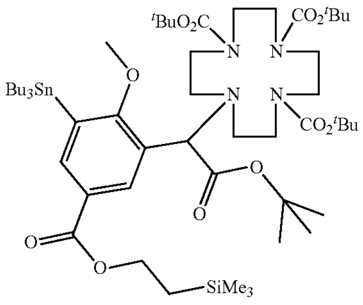

-continued

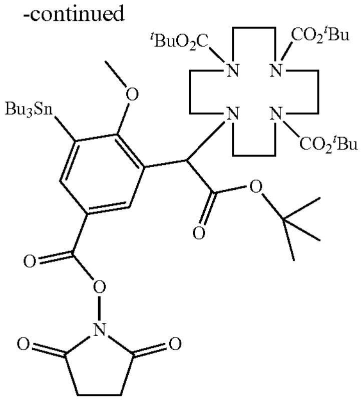

A round bottom flask was charged with tri-tert-butyl 2,2',2"-(10-(1-(3-bromo-2-methoxy-5-((2-(trimethylsilyl) ethoxy)carbonyl)phenyl)-2-(tert-butoxy)-2-oxoethyl)-1,4,7,10-tetraazacyclododecane-1,4,7-triyl)triacetate (444 mg, 1 eq., 463 μmol), 1,4-Dioxane (20 mL) and 1,1,1,2,2,2-hexabutyldistannane (1.34 g, 5.0 eq., 2.32 mmol) and the solution was allowed to stir at 100° C. for 15 minutes. The reaction mixture was then mixed with bis(triphenylphosphine)palladium (II) chloride (65.1 mg, 0.2 eq., 92.7 μmol) and the reaction was allowed to proceed for a total of about 6.0 hours. The reaction mixture was poured over ice and partitioned between EtOAc and water. The black mixture was filtered through Celite and the filter cake was washed with additional EtOAc. The organics were separated and dried over $MgSO_4$ followed by concentration. The crude oil was filtered through a pad of silica gel and eluted with (hexanes: EtOAc (5:1)) to give tri-tert-butyl 2,2',2"-(10-(2-(tert-butoxy)-1-(2-methoxy-3-(tributylstannyl)-5-((2-(trimethylsilyl)ethoxy)carbonyl)phenyl)-2-oxoethyl)-1,4,7,10-tetraazacyclododecane-1,4,7-triyl)triacetate (243 mg, 44.9%) as a crude oil contaminated with hexabutylditin. LRMS (M+Na) (1191, 1189, 1192, 1187, 1188).

m. Tri-tert-butyl 2,2',2"-(10-(2-(tert-butoxy)-1-(5-(((2,5-dioxopyrrolidin-1-yl)oxy)carbonyl)-2-methoxy-3-(tributylstannyl)phenyl)-2-oxoethyl)-1,4,7,10-tetraazacyclododecane-1,4,7-triyl)triacetate

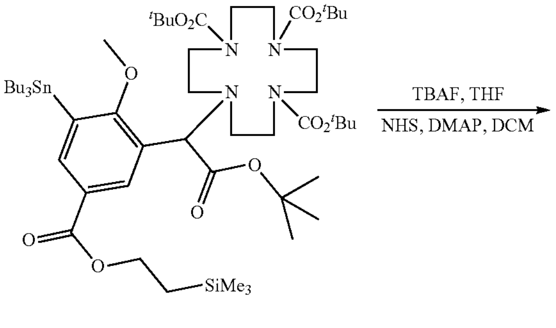

To an oven dried round bottom flask was added tri-tert-butyl 2,2',2"-(10-(2-(tert-butoxy)-1-(2-methoxy-3-(tributylstannyl)-5-((2-(trimethylsilyl)ethoxy)carbonyl)phenyl)-2-oxoethyl)-1,4,7,10-tetraazacyclododecane-1,4,7-triyl) triacetate (200 mg, 1 eq., 171 μmol), anhydrous tetrahydrofuran (10 mL) and TBAF (179 mg, 0.68 mL, 4.0 eq., 685 μmol. The reaction stirred at rt for a period of 72 hours and was monitored by TLC. After 72 hours the reaction mixture was concentrated to dryness. The crude mixture was re-dissolved into anhydrous dichloromethane (20 mL) and mixed with 1-hydroxypyrrolidine-2,5-dione (98.5 mg, 5.0 eq., 856 μmol), DMAP (20.9 mg, 1 eq., 171 μmol) and EDC (328 mg, 10 eq., 1.71 mmol). The resulting homogeneous solution was stirred at rt for a period of 64 hours and was concentrated to dryness. The resulting oil was partitioned between ethyl acetate and water. The water was separated, discarded and the organics were washed with additional saturate NaCl. The organics were dried with anhydrous $Na_2SO_4$ and concentrated to dryness. The crude foamy solid was chromatographed using flash chromatography (9:1 $CH_2Cl_2$: MeOH). The resulting fractions were then re-chromatographed using preparative TLC. The bands containing the product were isolated and mixed with a 9:1 $CH_2Cl_2$: MeOH mixture and filtered to remove the silica gel. The solvent was removed in vacuo to give tri-tert-butyl 2,2',2"-(10-(2-(tert-butoxy)-1-(5-(((2,5-dioxopyrrolidin-1-yl)oxy)carbonyl)-2-methoxy-3-(tributylstannyl)phenyl)-2-oxoethyl)-1,4,7,10-tetraazacyclododecane-1,4,7-triyl)triacetate (18 mg, 8.1%) as a semi-solid. LRMS (M+Na), (1188, 1186, 1189, 1187, 1184).

All publications, patents and patent applications mentioned in the specification are indicative of the level of those skilled in the art to which this invention pertains. All publications, patents and patent applications are herein incorporated by reference to the same extent as if each individual publication, patent or patent application was specifically and individually indicated to be incorporated by reference. Although the foregoing invention has been described in some detail by way of illustration and example for purposes of clarity of understanding, it will be obvious that certain changes and modifications may be practiced within the scope of the embodiments.

What is claimed is:

1. A radiohalogen prosthetic moiety or precursor thereof represented by the following formula:

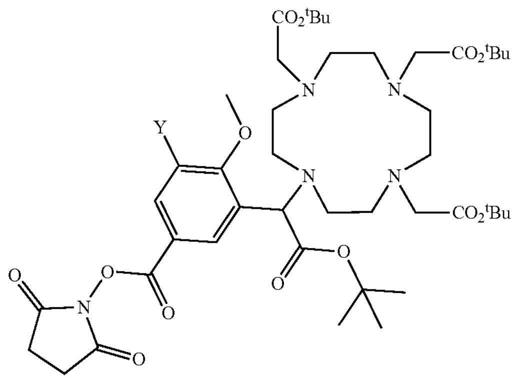

wherein:

Y is a radioactive halogen or a trialkyl tin precursor to a radioactive halogen.

2. A radiohalogen prosthetic moiety or precursor thereof represented by the following formula:

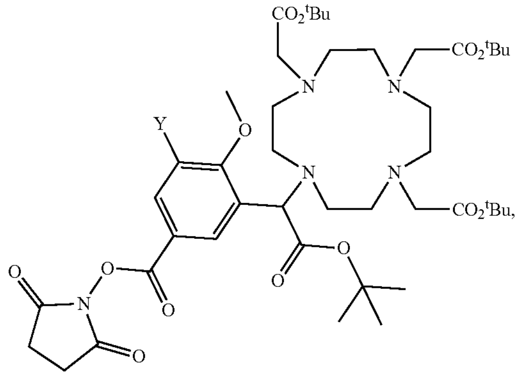

wherein Y is a radioactive halogen.

3. The radiohalogen prosthetic moiety or precursor thereof of claim 1, wherein Y is selected from the group consisting of $^{18}$F, $^{75}$Br, $^{76}$Br, $^{77}$Br, $^{123}$I, $^{124}$I, $^{125}$I, $^{131}$I, and $^{211}$At.

4. The radiohalogen prosthetic moiety or precursor thereof of claim 1, wherein Y is the trialkyl tin is a trialkyl tin precursor to a radioactive halogen.

5. A radiohalogen prosthetic moiety represented by the following formula:

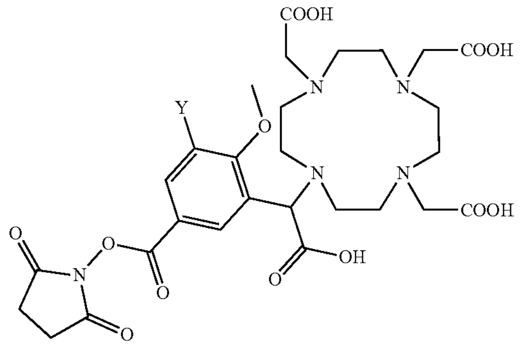

wherein Y is a radioactive halogen.

6. A radiolabeled biomolecule or intermediate, comprising the radiohalogen prosthetic moiety or precursor thereof of claim 1 attached to a biomolecule.

7. The radiolabeled biomolecule or intermediate of claim 6, wherein the biomolecule is selected from the group consisting of an antibody, an antibody fragment, a VHH molecule, an aptamer or variations thereof.

8. The radiolabeled biomolecule or intermediate of claim 6, wherein the biomolecule is the VHH molecule.

9. The radiolabeled biomolecule or intermediate of claim 8, wherein said VHH molecule targets HER2.

10. The radiolabeled biomolecule or intermediate of claim 6, wherein the biomolecule comprises a carbamate- or urea-containing pharmacological moiety.

11. The radiolabeled biomolecule or intermediate of claim 10, wherein the carbamate- or urea-containing pharmacological moiety is a moiety used to target PSMA on prostate cancer.

12. The radiohalogen prosthetic moiety or precursor thereof of claim 1, wherein Y is $^{131}$I.

13. The radiohalogen prosthetic moiety or precursor thereof of claim 2, wherein Y is selected from the group consisting of $^{18}$F, $^{75}$Br, $^{76}$Br, $^{77}$Br, $^{123}$I, $^{124}$, $^{125}$I, $^{131}$I, and $^{211}$At.

14. The radiohalogen prosthetic moiety or precursor thereof of claim 2, wherein Y is $^{131}$I.

15. The radiohalogen prosthetic moiety of claim 5, wherein Y is selected from the group consisting of $^{18}$F, $^{75}$Br, $^{76}$Br, $^{77}$Br, $^{123}$I, $^{124}$I, $^{125}$I, $^{131}$I, and $^{211}$At.

16. The radiohalogen prosthetic moiety of claim 5, wherein Y is $^{131}$I.

17. The radiohalogen prosthetic moiety of claim 5, further comprising a metal complexed by the polydentate chelate moiety of the formula.

18. The radiohalogen prosthetic moiety of claim 17, wherein the metal is selected from the group consisting of nonradioactive lutetium, yttrium, indium, and gallium, and radioactive $^{177}$Lu, $^{64}$Cu, $^{67}$Cu, $^{111}$In, $^{90}$Y, $^{225}$ Ac, $^{213}$Bi, $^{212}$Pb, $^{212}$Bi, $^{67}$Ga, $^{68}$Ga, $^{89}$Zr, and $^{227}$Th.

* * * * *